(12) United States Patent
Kantrowitz et al.

(10) Patent No.: US 10,321,725 B2
(45) Date of Patent: Jun. 18, 2019

(54) INFECTION CONTROL GLOVE WITH SENSORY CONTAMINATION INDICATOR

(76) Inventors: Allen B. Kantrowitz, Miami Beach, FL (US); In Ki Mun, Nanuet, NY (US)

(*) Notice: Subject to any disclaimer, the term of this patent is extended or adjusted under 35 U.S.C. 154(b) by 455 days.

(21) Appl. No.: 13/281,892

(22) Filed: Oct. 26, 2011

(65) Prior Publication Data

US 2013/0104284 A1    May 2, 2013

(51) Int. Cl.
| | |
|---|---|
| A41D 19/00 | (2006.01) |
| A61B 17/00 | (2006.01) |
| A61B 42/00 | (2016.01) |
| A61B 42/40 | (2016.01) |
| A61B 90/40 | (2016.01) |

(52) U.S. Cl.
CPC .......... *A41D 19/0031* (2013.01); *A61B 42/00* (2016.02); *A61B 42/40* (2016.02); *A61B 90/40* (2016.02); *A41D 19/0058* (2013.01); *A41D 2400/32* (2013.01); *A41D 2400/34* (2013.01); *A41D 2400/52* (2013.01); *A61B 2017/0003* (2013.01); *A61B 2017/00115* (2013.01); *A61B 2017/00119* (2013.01)

(58) Field of Classification Search
CPC ...... A41D 19/015; A61B 19/04; A61B 19/041
USPC ......................................... 2/159, 160, 161.7
See application file for complete search history.

(56) References Cited

U.S. PATENT DOCUMENTS

| | | | |
|---|---|---|---|
| 4,696,065 A | 9/1987 | Elenteny | |
| 4,773,532 A * | 9/1988 | Stephenson | 206/278 |
| 4,956,635 A * | 9/1990 | Langdon | A61B 19/041 |
| | | | 340/540 |
| 5,204,632 A * | 4/1993 | Leach | 324/557 |
| 5,357,636 A | 10/1994 | Dresdner, Jr. et al. | |
| 5,448,177 A * | 9/1995 | Thompson | A61B 19/041 |
| | | | 324/556 |
| 5,467,483 A | 11/1995 | Saadatmanesh et al. | |
| 5,483,697 A | 1/1996 | Fuchs | |
| 5,785,181 A | 7/1998 | Quartararo, Jr. | |
| 7,805,214 B2 | 9/2010 | Yamauchi et al. | |
| 7,972,437 B2 | 7/2011 | Alivisatos et al. | |
| 8,578,519 B2 | 11/2013 | Kantrowitz | |

(Continued)

FOREIGN PATENT DOCUMENTS

| | | | |
|---|---|---|---|
| GB | 2289616 A | * | 11/1995 |
| GB | 2446871 A | | 8/2008 |

(Continued)

OTHER PUBLICATIONS

O'Boyle, Carol A. et al., "Understanding Adherence to Hand Hygiene Recommendations: The Theory of planned Behavior", American Journal of Infection Control, Dec. 2001, pp. 352-360, vol. 29, Issue 6, copyright © 2001 by the Association for Professionals in Infection Control and Epidemiology, Inc.; doi:10.1067/mic.2001.118405.

(Continued)

Primary Examiner — Sally Haden
(74) Attorney, Agent, or Firm — Avery N. Goldstein; Blue Filament Law PLLC

(57) ABSTRACT

A barrier protection device and dispensing system are provided in the form of a medical service or examination glove with sensory indicators that respond to contact with infectious agents or substances. The glove and dispensing system prevent transmission of infectious agents from a healthcare worker to a patient or vice versa.

13 Claims, 4 Drawing Sheets

(56) References Cited

U.S. PATENT DOCUMENTS

| | | |
|---|---|---|
| 2005/0002995 A1 | 1/2005 | Schaller |
| 2006/0059603 A1 | 3/2006 | Peng |
| 2008/0040834 A1 | 2/2008 | Schaller et al. |
| 2008/0073388 A1 | 3/2008 | Saegusa |
| 2008/0171311 A1* | 7/2008 | Centen et al. ................ 434/265 |
| 2010/0097195 A1* | 4/2010 | Majoros et al. ............. 340/10.6 |
| 2010/0231385 A1 | 9/2010 | Melker et al. |

FOREIGN PATENT DOCUMENTS

| | | |
|---|---|---|
| GB | 2464362 A | 4/2010 |
| GB | 2466638 A | 7/2010 |
| KR | 1020090120362 A | 11/2009 |
| WO | 2010056534 A2 | 5/2010 |
| WO | WO 2011/146061 A1 | 11/2011 |

OTHER PUBLICATIONS

Gallagher, M. et al., "Analyses of Volatile Organic Compounds From Human Skin", British Journal of Dermatology, Sep. 17, 2008, pp. 780-791, vol. 159, Issue 4; Author Manuscript; available in PMC Sep. 1, 2009, 26 pages, © 2008 British Association of Dermatologists; doi:10.1111/j.1365-2133.2008.08748.x.

* cited by examiner

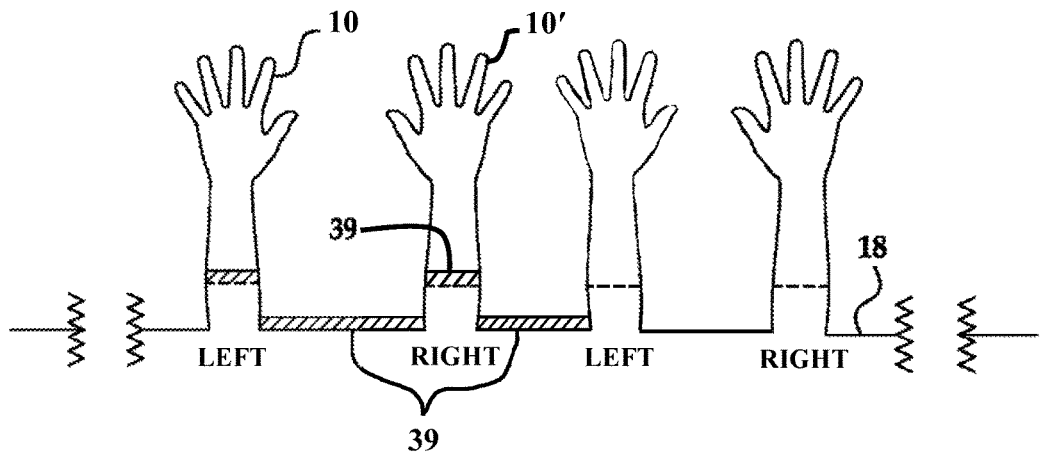
FIG. 2A
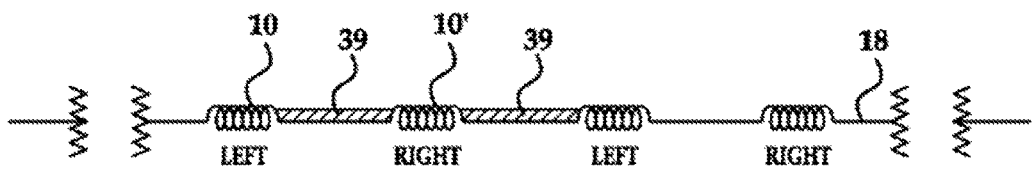
FIG. 2B
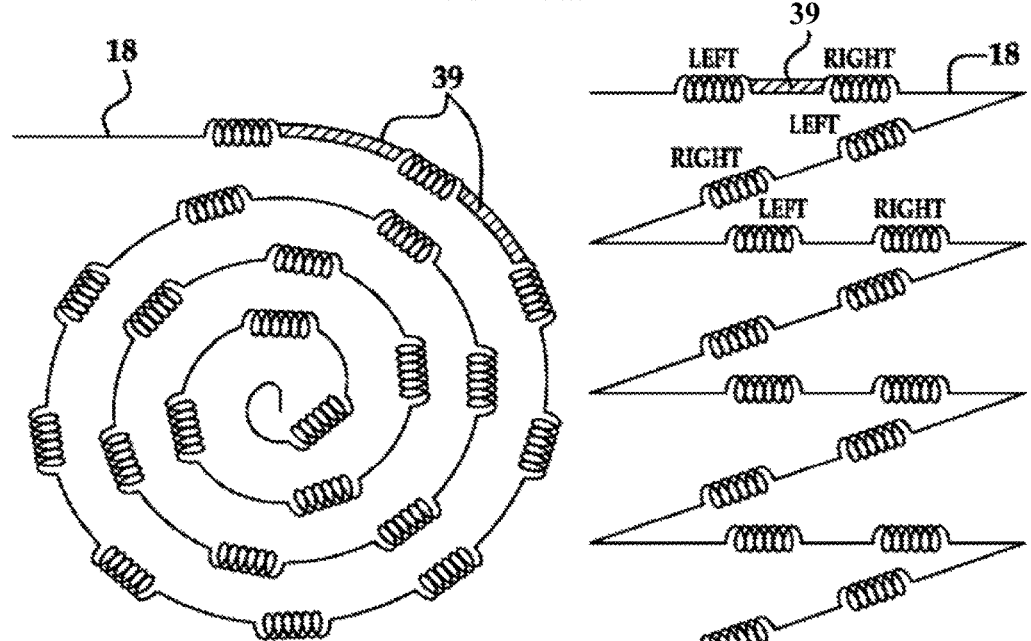
FIG. 2C
FIG. 2D

INFECTION CONTROL GLOVE WITH SENSORY CONTAMINATION INDICATOR

FIELD OF THE INVENTION

The present invention in general relates to infection control and prevention and in particular to a glove with sensory indicators that respond to contact with infectious agents or substances.

BACKGROUND OF THE INVENTION

Nosocomial infections, commonly referred to as hospital-acquired infections, are responsible for the deaths of tens of thousands of people each year. Nosocomial infections, are unrelated to a patient's initial hospital admission diagnosis, but are infections acquired during the patients stay or visit to a health care facility. Nosocomial infections due to resistant organisms represent a serious problem. Microbes can acquire resistance to antibiotics, antifungals, and antivirals and as the numbers of resistant organisms increase, the number of new antimicrobial agents to treat them has not kept pace. In fact, community acquired nosocomial infections, especially methicillin resistant *staphylococcus aureus* (MRSA), has increased at an alarming rate. In the United States, it has been estimated that as many as one hospital patient in ten acquires a nosocomial infection, or 2 million patients a year. Studies have shown that at least one third of nosocomial infections are preventable, but the problem of infection persists.

Reports indicate that more than 50% of all nosocomial infections can be directly related to the transmission of harmful bacteria by healthcare workers who have not properly washed their hands before and after each patient contact. Thus, an efficient way to reduce transfer of these organisms from patient-to-patient and to reduce the emergence of resistant organisms is hand washing with soap and water between patient contacts.

Despite the fact that numerous strategies have been attempted to increase healthcare worker compliance to hand washing, and the Centers for Disease Control and Prevention (CDC) as well as other regulatory agencies recommend hand washing before and after each patient encounter, reports indicate that healthcare workers adhere to hand washing guidelines less than 70% of the time (see O'Boyle, C. A. et al., "Understanding adherence to hand hygiene recommendations: the theory of planned behavior," Am J Infect Control., 29 (6):352-360 (2001)). Alternatively to, or in addition to, hand washing, barrier protection in the form of gloves provide mechanical and microbial isolation between the patient and health care worker. As is true of hand-washing, there exists poor compliance with glove-based safety protocols.

The high rate of non-compliance to infection control procedures, such as hand washing and wearing a new pair of protective gloves between patients, by healthcare workers is an indication of the failure of the existing approaches to hand washing stations and audit procedures. As such, there is a need for improved mechanisms for infection control and prevention that will increase user compliance and simultaneously decrease the risk or prevalence of transmission of infectious agents from a healthcare worker to a patient or vice versa.

SUMMARY OF THE INVENTION

Barrier protection in the form of a medical service or examination glove with sensory indicators that respond to contact with infectious biological agents or substances, and a dispensing device for the glove are provided to prevent transmission of infectious agents from a healthcare worker to a patient or vice versa.

Embodiments of the medical service- or examination-glove provide a sensory indication of a color change (e.g., green to red or no color to colored) when a glove surface has contacted human or animal skin or other contaminated surfaces, or if the glove has been donned for a measured period of time, or if the donned glove has been geographically moved between permissible and non-permissible locations within the topography of the health care setting, or if a defect has occurred in the barrier function or structure of the glove. In a preferred embodiment, an unambiguous change is noted to facilitate patient's ability to monitor and refuse health worker contact until clean gloves or at least removal of the tainted or expired gloves occurs. Additionally, family members as well as other health care workers are enabled by the invention to participate in policing of glove status. Glove attributes that promote identification of tainted gloves include: binary color change, an auditory alarm, large glove area color change in response to even localized forbidden contact, and combinations thereof. In addition to being detectable by patients, auditing and monitoring systems, such as video systems in a patient room or geographical coordinate determination systems, may also detect tainted gloves approaching a patient thereby augmenting the policing of glove status and adherence to facilities' policies and procedures.

Embodiments of the inventive barrier protection and dispensing device overcome deficiencies in current hand washing auditing and monitoring systems by extending infection prevention awareness to patients, their visitors as well as nearby health care professionals. Patients and their visitors are educated to note the sensory indications on their caregiver's gloves prior to having the caregiver touch the patient's body, items to be ingested or medical equipment associated with the patient. Thus, patients and their visitors are taught to police the policy of barrier protection between worker and patient, thereby providing a secondary and active means to ensure compliance to good sanitary practices. A process of inhibiting nosocomial infection in a patient by a health worker is provided in which the patient or a visitor is alerted to refuse contact by a gloved health care worker when the sensory indicator associated with the glove has changed in response to contact with the forbidden surface, presence in a geographic exclusion zone, the expiration of a preselected wear time period, or glove barrier compromise. The health care worker then removes the tainted glove in response to the refusal of contact by the patient prior to contacting the patient. The donning of a second, unused protective barrier is ideal, but simply by removing the contaminated barrier nosocomial infective agent transfer is reduced.

An embodiment of a dispenser for providing invaginated gloves with monitoring capabilities is also provided.

BRIEF DESCRIPTION OF THE DRAWINGS

FIG. 2A is a perspective view of the inventive barrier glove of FIG. 1A in an expanded state on a continuous ribbon for use in the dispensing device of FIG. 3;

FIG. 2B is a perspective view of the inventive barrier glove of FIG. 1A in an invaginated or folded state on a continuous ribbon for use in the dispensing device of FIG. 3;

FIG. 2C is a perspective view of the continuous ribbon of FIG. 2B in a roll;

FIG. 2D is a perspective view of the continuous ribbon of FIG. 2B in a fan fold;

DETAILED DESCRIPTION OF THE PREFERRED EMBODIMENTS

Figure 1A:
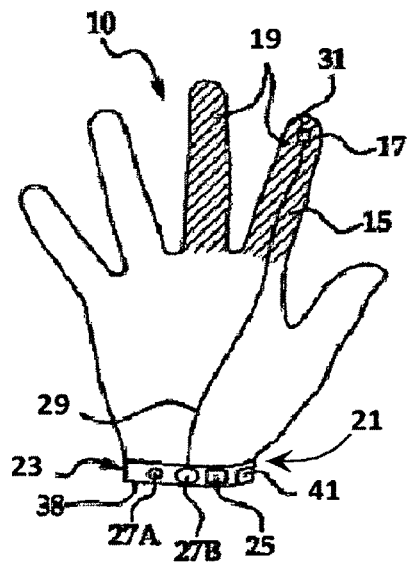
FIG. 1A is a perspective view of an inventive barrier glove with sensory contamination indicators prior to use.

The following description of particular embodiment(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention, but are presented for illustrative and descriptive purposes only.

Barrier protection in the form of a medical service or examination glove with sensory indicators that respond to contact with infectious agents or substances with an optional integral remote-sensing/communication tag, and a dispensing device for the glove are provided to prevent transmission of infectious agents from a healthcare worker to a patient or vice versa. The aforementioned optional integral remote-sensing, communication, or both attributes in a tag operated with a device that senses based on electrical, mechanical, acoustic, chemical, optical or a combination of such attributes and is integrated into the glove structure as an embedded, attached, or associated tag. The tag optionally provides for enhanced functionality in one or more of several forms including: geographic position sensing, timing sensing, sensing of nearby tags, temperature sensing, sensing of additional sensing elements of the same glove, or remote communication capability.

Embodiments of the present invention relating to glove compromise, conductivity is measured by electrical sensors coupled across the interior and exterior surfaces of the glove to monitor conductivity therebetween. With compromise of the glove and contact with a conductive surface of a conductivity greater than that of ambient air, a conductivity increase is noted. A sensory indicator associated with the glove responsive to the electrodes is triggered as an alert of glove integrity compromise. It is appreciated that the glove sensory indicator operates as an alert beacon that is attached to the glove, as a physically separate bracelet, or an apparel accoutrement.

In a contact sensitive temporal duration embodiment, the glove exterior has a contact electrode that is activated by contact with a conductive surface, such as human skin to initiate a count down timer for a time-based glove exchange alert, as further detailed below.

Embodiments of the medical service or examination glove provide as a sensory indicator as a color change (e.g., green to red or no color to colored) when an external glove surface has contacted animal skin or if geographic exclusion has been breached, or a time wear criterion has been met, or the integrity of the glove barrier been comprised, or combination thereof. In addition to being detectable by patients, a remote sensing auditing/monitoring system such as a video or audio system in a patient room could also detect tainted gloves approaching a patient. Patients and their visitors are educated to observe the sensory indications on their caregiver's gloves prior to having the caregiver touch the patient's body or items to be ingested or prone to harbor infectious agents associated with patient care. Thus, patients, their visitors, and health care worker peers are taught to police the policy of barrier protection between worker and patient, thereby providing a secondary and active means to ensure compliance to good sanitary practices. As used herein, a "medical appliance" is defined as an invasive article, or article that is brought into physical contact or proximity to a patient.

In a temporal embodiment, a health care worker wears a bracelet or other accoutrement including an inventive tag associated with gloving behavior, the tag emitting a given light (e.g., green) or other signal such as auditory and electronic when the worker dons gloves and a button activates to initiate a permissible wear period for a glove is activated. After a preselected time, the tag light changes to alert the worker, their co-workers, and patient that the gloves have been worn beyond a preselected duration and a glove change is in order. Representative tag light changes illustratively include: a color change, (e.g., green to red), periodicity (e.g., continuous to pulsed emission), and a combination thereof. It is appreciated that an LED is well suited as a light indicator for such a tag. Optionally, an auditory alarm is also provided as a separate or additional sensory indicator. In operation, a worker, patient, or visitor notes the tag status from the bracelet or other accoutrement and assures that the gloves are sufficiently new to be within the preselected wearing threshold. While this embodiment alone does not respond per se to forbidden surface contact, initial testing shows that nosocomial infection rates decline by more than twenty percent in a conventional general ward through usage of this temporal invention embodiment. Studies have shown that human skin emits a variety of volatile metabolic compounds (see Gallagher, M. et al., "Analyses of volatile organic compounds from human skin," NIH Public Access (2008)) that are readily detectable. In embodiments, one or more sensors on a gloves surface are sensitive to skin chemistry and activate an LED, dye pack, surface bound dye, superparamagnetic particle or other indicators to signal contact with a patient's skin. In embodiments, an enzyme or other reactive elements on the surface of glove creates a color change upon contact with a skin emitted chemical such as octen-3-ol, methlyphenol, etc., that cause a chemical reaction that creates a color change as the sensory indicator.

Figure 1B:
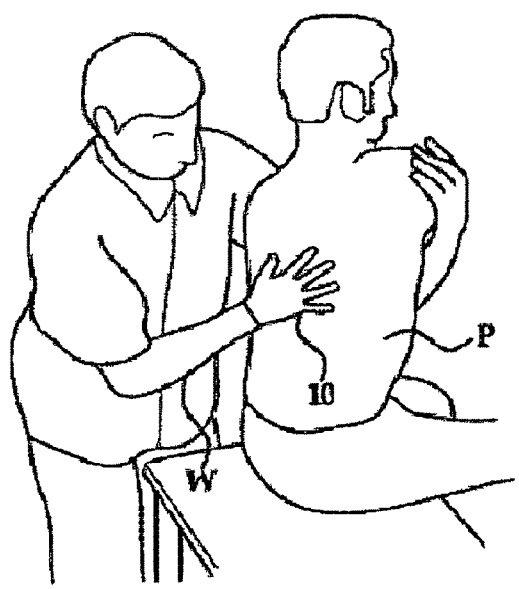
FIG. 1B is a perspective view of the inventive barrier glove of FIG. 1A in use and in contact with a patient's skin or other forbidden surface such as dressings, clothing or bed sheets.
Figure 1C:
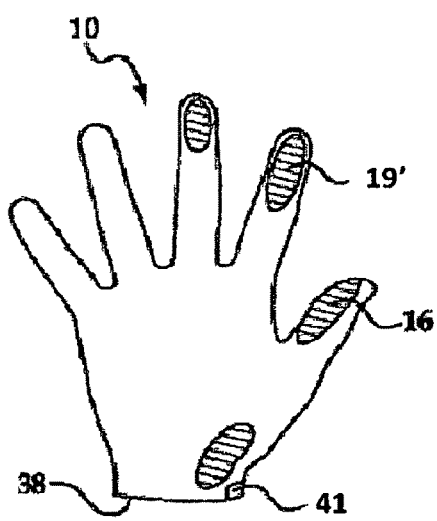
FIG. 1C is a perspective view of the inventive barrier glove of FIG. 1A were only areas of the glove that were in contact with the patient's skin or contaminated surface change.
Figure 1D:
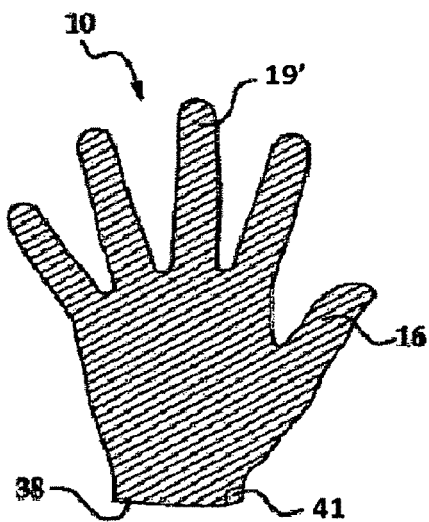
FIG. 1D is a perspective view of the inventive barrier glove of FIG. 1A were the entire surface of the glove changes when in contact with the patient's skin or contaminated surface or if the geographic exclusion or timing criteria have been met.

Referring now to FIGS. 1A-1D, an inventive barrier protection glove is depicted generally at 10. The exposed outer surface of the glove 10 is optionally treated with a reactive element that is sensitive to glove exterior contact with human or animal skin or other forbidden organisms. In FIG. 1A the glove 10 is in an unused state and has a given color and forbidden surface, or electrodes to measure transbarrier conductance, thereby indicating the glove 10 has not been in contact with other people or is otherwise in a precluded condition for patient contact. In FIG. 1B, the glove 10 is now being worn by a healthcare worker W who is touching and assisting a patient P. In FIG. 1C specific areas of the outer surface of glove 10 that were in contact with the patient's P skin or other forbidden surface change to a different color or condition, thereby alerting the health care worker W, their peers, and future patients who have contact with the healthcare worker that the gloves 10 need to be changed prior to interacting with the next patient or handling sensitive items prone to cause infections for the next patient. In FIG. 1D the entire outer surface of glove 10 changes color or pattern in response to contact with a patient's skin or other forbidden surface.

With reference to FIG. 1A, a composite of various components is provided with the understanding that less than the complete set of these components is needed to achieve the inventive benefits to promote hygienic, clean-gloved contact of a patient by a health care worker; an electrode 17 is attached to the exterior surface 15 of the glove 10. A sensory indicator is shown at 19 adhered to the glove 10 as a colorimetric material that changes color as depicted in FIGS. 1C and 1D as depicted at 19'. An electrically powered sensory indicator 23 is provided with a power supply 25 and an optical beacon 27A such as an LED and/or an auditory beacon 27B to provide a sensory alert to a bystander and the wearer of the glove 10. The electrically powered sensory indicator 23 is optionally provided as a bracelet 21 or other apparel accoutrement. Communication provided between an electrode 17 and an the attached electrically powered indicator 23 or a detached indicator is by electrical wires 29 or by wireless communication through an RFID tag 31 associated with the glove 10 and a receiver in electrical communication with the detached indicator. As noted above an optional integral remote-sensing/communication tag may also be provided.

The notification that a glove has previously contacted a forbidden surface prior to patient contact is critical to preventing infective agent transmission from a first patient to a second patient in a medical setting. Preferably, a glove having contacted a forbidden surface undergoes a colorimetric change either on the glove surface or through a sensor that initiates emission of a light or auditory signal indicative of is unsuitable for contact with a patient.

While glove contact with skin as a forbidden surface is readily detected through a chemical reaction associated with human metabolic processes such as molecules emitted by the skin associated with bacteria on the skin either through the use of sensors or immunochemistry conventional to the art to trigger a reaction that is preferably both colorimetric and irreversible; creating such a reaction through contact with a designated inanimate surface through creating a marker associated with the forbidden surface is more involved. Marking of the surface to designate the same as forbidden prior to patient contact includes coding the surface with a dye or other substance that is transferred to the glove upon contact therebetween, or rendering the surface conductive relative to air to trigger a conductivity measurement.

A dye is detected under visible or ultraviolet or infrared light in the case of a passive transfer. In other instances, the surface dye is a reagent that is modified by reaction with a substance on the glove surface. By way of example, a glove outer surface is treated with a dye precursor such as a polyaminoacid nitroanilide (E.G.D-Val-Leu-Lys-p-nitroanilide HCl or pyroGlu-Leu-Lys-p-nitroanilide HCl) is cleaved by a variety of a specific enzymes commonly found on surfaces through the presence of various organisms to induce a colorimetric change. Alternatively, a glove is coated with super paramagnetic colloidal nanocrystals per U.S. Pat. No. 7,972,437 and generates a color change through a magnetic field of sufficient strength being generated in proximity to the forbidden surface or geographic exclusion zone. Still another process for inducing a color change is through recordation of an electrical contact being formed between the forbidden surface, optionally overlaid with electrical contacts, and the glove; or an or RFID signal or an optical signal communicated from a sensor associated with the glove when the glove is brought into proximity with a forbidden surface. Additionally, a position monitoring network is also set up to establish when a glove has moved from a geographic exclusion zone into proximity to a patient with a visual, auditory or combination of such signals being triggered by such an event. Such a proximity position monitoring network is detailed in U.S. Pat. No. 5,785,181.

Figure 3:
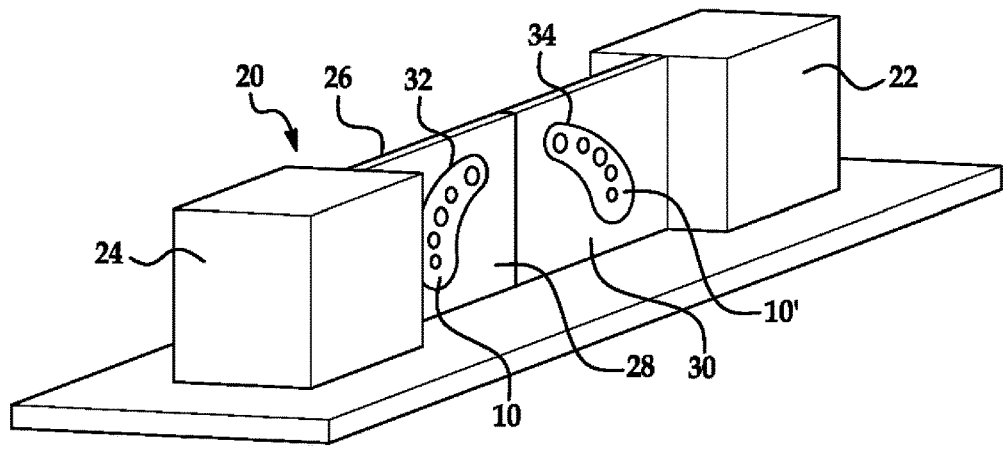
FIG. 3 is a perspective view of a glove dispenser according to embodiments of the invention.

FIGS. 2A-2D illustrate the glove 10 assembled in feed ribbon for use in an inventive dispenser 20 as depicted in FIGS. 3 and 4. In FIG. 2A, the barrier glove 10 of FIG. 1A is in an expanded state on a continuous ribbon 18 for use in the dispensing device 20 of FIG. 3. The glove 10 is arranged as left (10) and right (10') pairs on the continuous ribbon 18. Optionally, a radio frequency identification (RFID) tag 41 or bracelet 21 may be secured to a cuff 38 of the glove 10 as disclosed in U.S. Utility application Ser. No. 12/959,782 filed 3 Dec. 2010 and entitled, "SURGICAL GLOVE APPLIANCE DEVICE", the contents of which are incorporated herein by reference. In an embodiment, rib stiffeners 39 are integrated into the continuous ribbon 18 to facilitate engagement of the continuous ribbon 18 into a supporting frame 26 (see FIG. 3) of the dispensing device 20. FIG. 2B illustrates the barrier gloves 10 and 10' of FIG. 2A in an invaginated or folded state on a continuous ribbon for use in the dispensing device of FIG. 3. Methods for folding the glove 10 are also described in U.S. Utility application Ser. No. 12/959,782 that as previously stated is incorporated herein by reference. FIGS. 2C and 2D illustrate the continuous ribbon 18 in a roll or fan folded, respectively for ease of storage, distribution, packing, and for loading into the dispenser 20.

FIG. 3 is a perspective view of a glove dispenser 20 according to embodiments of the invention. The glove dispenser 20 has a source container 22 to hold a feed stock of the continuous ribbon 18 that holds the left (10) and right (10') alternating pairs of glove 10. The supporting frame 26 engages the continuous ribbon 18, and faceplates 28 and 30 provide an indication to a user to insert their hands into hand passages 32 and 34 of the left 10 and right 10' gloves. Empties container 24 provides a take up reel for collecting the used ribbon stock that held the gloves 10. The take up reel may be motorized to automatically advance the glove pairs (10, 10') for the next user. The hand passages 32 and 34 may either be horizontally or vertically mounted and the dispenser 20 may be mounted on a wall adjacent to a doorway, hand washing sink, bedside or the edge of a bed. It is appreciated that a retainer ring stiffener 39 to facilitate hand insertion into the glove 10 clamps onto the cuff 38 of the glove 10 to reuse this component and allow more efficient glove storage in a container 22. The dispenser 20 can optionally charge a capacitor of the bracelet or embedded RFID tag of the gloves 10, as disclosed above at time of dispensing of the gloves 10. The dispenser 20 may optionally interrogate, correlate, and record the user's identification (ID) badge with the time and date of usage of the dispenser 20.

Figure 4A:
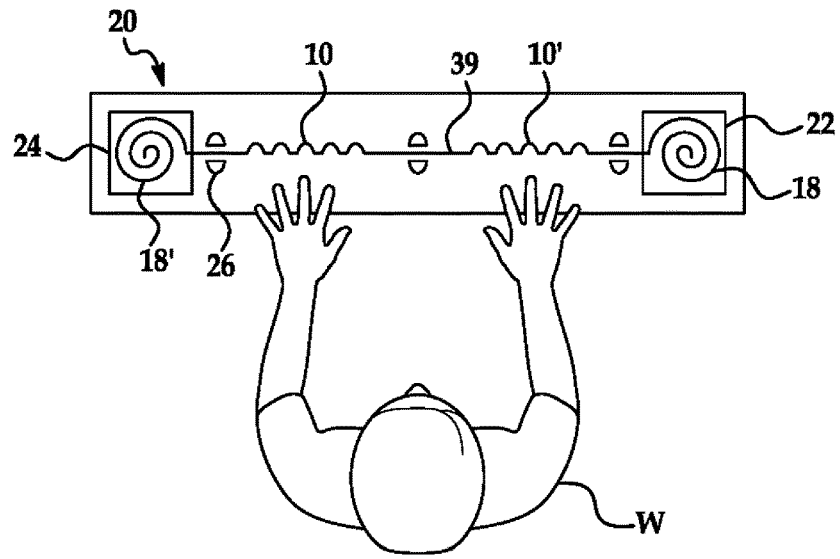
FIGS. 4A-4E are a top down perspective of the operation of the glove dispenser of FIG. 3.
Figure 4B:
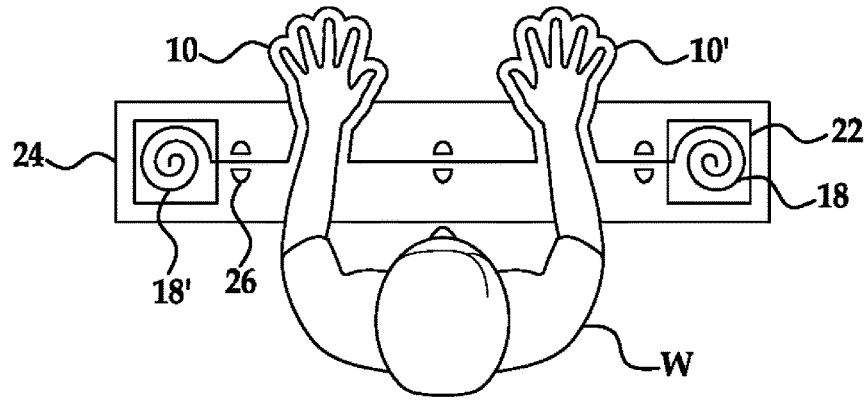
Figure 4C:
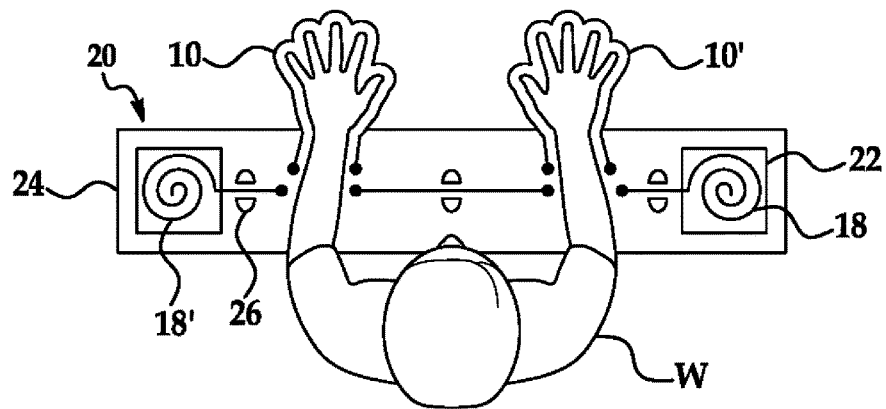
Figure 4D:
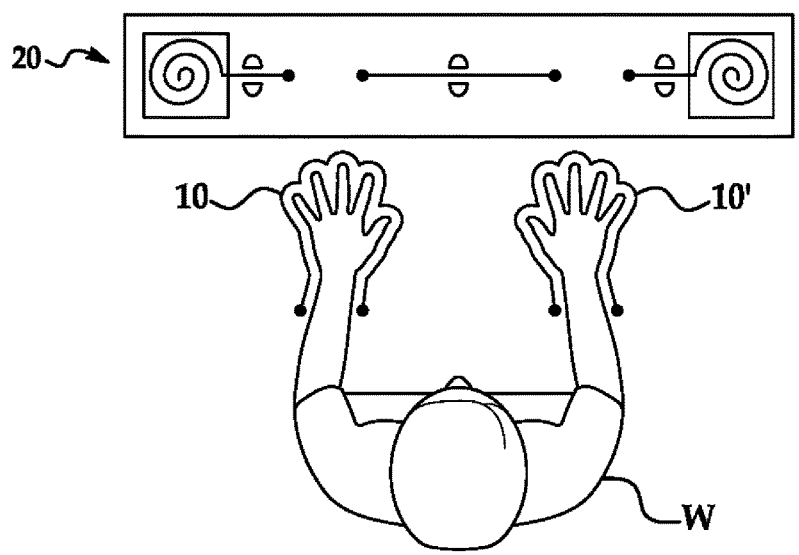
Figure 4E:
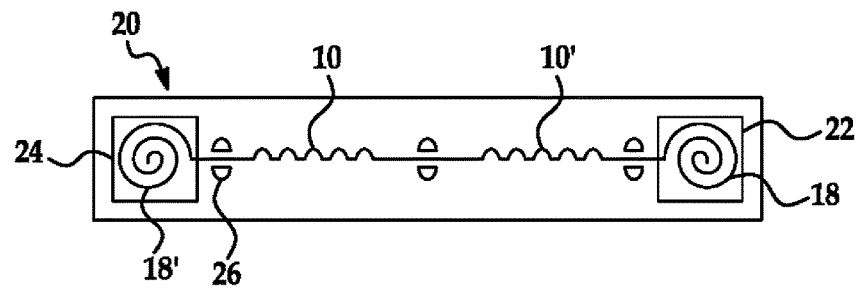

FIGS. 4A-4E provide a top down perspective of the operation of the glove dispenser of FIG. 3. In FIG. 4A, a healthcare worker approaches a dispenser 20 preloaded with rolled stock of continuous ribbon 18 that holds the left (10) and right (10') alternating pairs of invaginated glove 10. In FIG. 4B, the healthcare worker W inserts their hands through the hand passages 32 and 34, and their hands are engloved. Optionally, the ID of healthcare worker W is recorded by the dispenser 20. In FIG. 4C, the healthcare worker W continues to insert their hands into the gloves 10 until a pre-manufactured perforated perimeter 36 (see FIG. 2A) of the gloves (10, 10') separate from the continuous ribbon 18. In FIG. 4D, the healthcare worker W with their hands now fully engloved withdraws their hands from the dispenser 20. In FIG. 4E, the dispenser advances the continuous ribbon 18 for the next use. In an embodiment of the dispenser 20, usage events and inventory levels of the loaded gloves 10 are reported to a centralized management computer.

Optionally, the continuous feed mechanism and dispenser does not require invaginated gloves, but rather the dispenser assists in the act of glove donning by supporting an opened proto-glove in a fashion that facilitates donning.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A protective barrier device comprising:
    an examination glove having an external glove surface; and
    a sensory indicator associated with said examination glove, said sensory indicator being a dye precursor on the external glove surface, the dye precursor on the external glove surface changing color in response to the dye precursor on the external glove surface reacting with a skin emitted chemical to create a color change in the dye precursor upon contact with patient skin;
    the dye precursor being a polyamino acid nitroanilide.

2. The barrier device of claim 1 wherein said sensory indicator changes in response to contact with inanimate medical equipment.

3. The barrier device of claim 1 wherein said sensory indicator changes in response to contact with infectious agents that are found on the human.

4. The barrier device of claim 1 further comprising a conductivity electrode sensing an exterior surface of said glove, said conductivity electrode triggered in response to the exterior surface of said glove contacting substances with a conductivity greater than that of air.

5. The barrier device of claim 4 wherein said conductivity electrode is triggered in response to the exterior surface of said glove contacting infectious agents found on living human skin or on medical appliances.

6. The barrier device of claim 1 further comprising a radiofrequency identification (RFID) tag configured with a light emitting diode (LED); and
    wherein said LED is integrated into a bracelet or accoutrement, where the LED is activated upon at least one of: the expiration of a preselected glove wearing period or transit from geographic exclusion zones.

7. The barrier device of claim 6 wherein said light emitting diode (LED) upon activation under goes one or more of: a color change, a change in periodicity, or a combination thereof.

8. The barrier device of claim 6 wherein said RFID tag is configured with an auditory alarm.

9. The barrier device of claim 1 wherein said glove is part of a continuous ribbon.

10. The barrier device of claim 9 wherein said continuous ribbon has a series of right and left pairs, where said series of right and left pairs are in an invaginated or folded state on said continuous ribbon.

11. The barrier device of claim 9 wherein said continuous ribbon is formed into a roll.

12. The barrier device of claim 9 wherein said continuous ribbon is fan folded.

13. The barrier device of claim 9 wherein said continuous ribbon is mounted in a dispenser.

* * * * *